(12) United States Patent
Xu et al.

(10) Patent No.: US 11,597,915 B2
(45) Date of Patent: Mar. 7, 2023

(54) MATERIAL AND METHOD FOR PRODUCING CELL RECEIVING SCAFFOLD

(71) Applicant: Lung Biotechnology PBC, Silver Spring, MD (US)

(72) Inventors: Pingyong Xu, Valencia, CA (US); Luis Alvarez, Lexington, MA (US); Derek Morris, Somerville, MA (US); Iman Yazdi, Manchester, NH (US)

(73) Assignee: Lung Biotechnology PBC, Silver Spring, MD (US)

( * ) Notice: Subject to any disclaimer, the term of this patent is extended or adjusted under 35 U.S.C. 154(b) by 624 days.

(21) Appl. No.: 16/529,415

(22) Filed: Aug. 1, 2019

(65) Prior Publication Data
US 2020/0040306 A1 Feb. 6, 2020

Related U.S. Application Data

(60) Provisional application No. 62/713,817, filed on Aug. 2, 2018.

(51) Int. Cl.
| | |
|---|---|
| *B33Y 10/00* | (2015.01) |
| *C12N 5/09* | (2010.01) |
| *B33Y 70/00* | (2020.01) |
| *B29C 64/124* | (2017.01) |
| *B29L 31/00* | (2006.01) |
| *B33Y 80/00* | (2015.01) |
| *B29K 105/00* | (2006.01) |

(52) U.S. Cl.
CPC .......... *C12N 5/0693* (2013.01); *B29C 64/124* (2017.08); *B33Y 10/00* (2014.12); *B33Y 70/00* (2014.12); *B29K 2105/0002* (2013.01); *B29L 2031/7532* (2013.01); *B33Y 80/00* (2014.12); *C12N 2533/54* (2013.01)

(58) Field of Classification Search
CPC .... B33Y 80/00; B33Y 10/00; C12N 2533/54; C12N 5/0693; B29C 64/124
See application file for complete search history.

(56) References Cited

U.S. PATENT DOCUMENTS

2018/0230423 A1 8/2018 O'Mahony et al.

FOREIGN PATENT DOCUMENTS

| WO | WO 2014/088557 A1 | 6/2014 |
| WO | WO 2018/071639 A1 | 4/2018 |

OTHER PUBLICATIONS

Baek et al., "In situ assembly of the collagen-polyacrylamide interpenetrating network hydrogel: Enabling decoupled control of stiffness and degree of swelling," European Polymer Journal, Nov. 1, 2015, 72:413-422.

*Primary Examiner* — Larry W Thrower
(74) *Attorney, Agent, or Firm* — Foley & Lardner LLP

(57) ABSTRACT

A printable composition for the manufacture of cell-receiving scaffolds comprising about 0.3 wt % to about 3.0 wt % of one or more collagens; about 5.0 wt % to about 40.0 wt % of one or more monomers; about 0.5 wt % to about 2.0 wt % of a photo initiator; and 0 wt % to about 75 wt % of a vehicle comprising a protic solvent, by weight of the printable composition; wherein the printable composition has a resolution of about 100 microns or less when printed, a photo speed (Dp/Ec) of about 0.1-5 mm (Dp) and about 10-100 mJ/cm² (Ec) when printed, and a green strength of at least about 5 kPa after drying. The present technology further includes methods of manufacturing a three-dimensional cell-receiving scaffold using the printable composition.

4 Claims, 4 Drawing Sheets

MATERIAL AND METHOD FOR PRODUCING CELL RECEIVING SCAFFOLD

CROSS-REFERENCE TO RELATED APPLICATIONS

This application claims the benefit of U.S. Provisional Application No. 62/713,817, filed Aug. 2, 2018.

FIELD

The present technology relates generally to compositions and methods suitable for use as a printable material or inks. More particularly, and not by way of limitation, the present technology relates to printable compositions and methods suitable for obtaining three-dimensional cell-receiving scaffolds via three-dimensional printing methods.

BACKGROUND

Biological scaffolds are three-dimensional biomaterials before cells have been added, and are capable of receiving living cells. The scaffolds are used to provide a three-dimensional support and geometric structure for the cells. For example, one particular use of such biological scaffolds includes use as a replacement for functional human organs. This has been accomplished using suidae (e.g., pig) family sourced organs that are de-cellularized and then re-cellularized with compatible human cells. However, suidae family sourced scaffolds pose challenges, such as contamination from original suidae cells, bacteria, and other contaminants.

While three-dimensional printing technology can facilitate the production of three-dimensional scaffolds customized for a given subject, currently available systems with such printed scaffolds pose challenges, e.g., compatibility with implanted cells and achieving a high enough resolution to define walls or other features within the scaffold.

The present technology is directed to overcoming these and other deficiencies.

SUMMARY

In an aspect, a printable composition for the manufacture of cell-receiving scaffolds that includes about 0.3 wt % to about 3.0 wt % of one or more collagens; about 5.0 wt % to about 40.0 wt % of one or more monomers; about 0.5 wt % to about 2.0 wt % of a photo initiator; and 0 wt % to about 75 wt % of a vehicle comprising a protic solvent, by weight of the printable composition, where the printable composition exhibits a resolution of about 100 microns or less when printed, a photo speed (Dp/Ec) of about 0.1-5 mm (Dp) and about 10-100 mJ/cm$^2$ (Ec) when printed, and a green strength of at least about 5 kPa after drying.

In a related aspect of the present technology, a method is provided for preparing a three-dimensional cell-receiving scaffold using a printable composition as described herein in any embodiment. The method includes using the printable composition of any embodiment herein to fabricate a three-dimensional cell-receiving scaffold.

In another related aspect of the present technology, a method is provided for manufacturing a three-dimensional cell-receiving scaffold that includes depositing a layer of the printable composition as described herein in any embodiment to a surface to obtain a deposited layer, irradiating the deposited layer, and repeating the depositing and irradiating steps until the deposited layers form the three-dimensional cell-receiving scaffold, where the printable composition includes collagen, where the collagen is present in an amount from about 0.3 percent to about 3.0 percent by weight of the printable composition; a monomer; a photo initiator; and a vehicle. The printable composition may include a printable composition as described herein in any embodiment.

DETAILED DESCRIPTION

Figure 1:
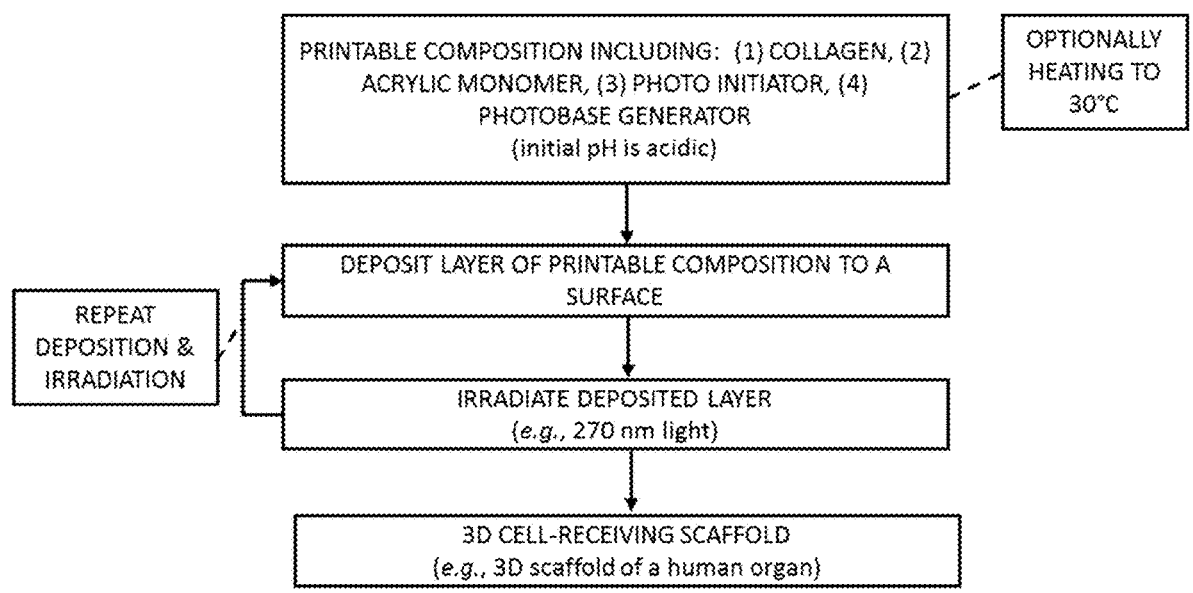
FIG. 1 illustrates a flowchart depicting an exemplary method for preparing a three-dimensional cell-receiving scaffold of the present technology

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The following terms are used throughout and are as defined below.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "collagen" refers to the main protein of connective tissue that has a high tensile strength and that has been found in most multicellular organisms. Collagen is a major fibrous protein, and it is also the non-fibrillar protein in basement membranes. It contains an abundance of glycine, proline, hydroxyproline, and hydroxylysine. Collagen is found throughout the body, and is of at least 12 types (type I-XII).

As used herein, the term "functionalized collagen" refers to collagen that has been modified to include one or more monomeric subunits attached to the collagen. The attached monomeric subunit allows the functionalized collagen to be photocurable, i.e., the monomeric subunits polymerize upon exposure to ultraviolet (UV), violet, or blue radiation.

As used herein, the term "non-functionalized collagen" refers to collagen that has not been modified to include one or more monomeric subunits. Non-functionalized collagen may not polymerize upon exposure to UV, violet, or blue radiation.

As used herein, the term "photobase generator" refers to an additive that responds to radiation by raising the pH of the printable composition. In some embodiments the printable composition can have an initially acidic pH which is then substantially neutralized in response to exposure to UV, violet, or blue radiation.

As used herein, the term "absorber" refers to an additive that absorbs radiation so as to control a "cure depth." This has the advantage of increasing resolution of the curative process. Absorbers can be dyes such as tartrazine.

The present technology provides printable compositions suitable for the preparation of three-dimensional cell-receiving scaffolds having a high resolution via manufacturing methods, such as 3D printing. In particular, the printable compositions are suitable for stereolithography.

The present technology provides printable compositions and methods for manufacturing three-dimensional cell-receiving scaffolds from the printable compositions. In certain aspects, the present technology relates to a printable composition. In another aspect, the present technology relates to methods of manufacturing a three-dimensional structure from the printable composition.

In an aspect, a printable composition for the manufacture of cell-receiving scaffolds that includes about 0.3 wt % to about 3.0 wt % of one or more collagens; about 5.0 wt % to about 40.0 wt % of one or more monomers; about 0.5 wt % to about 2.0 wt % of a photo initiator; and 0 wt % to about 75 wt % of a vehicle comprising a protic solvent, by weight of the printable composition, where the printable composition exhibits a resolution of about 100 microns or less when printed, a photo speed (Dp/Ec) from about 0.1-5 mm (Dp) and about 10-100 mJ/cm$^2$ (Ec) when printed, and a green strength of at least about 5 kPa after drying.

The term "resolution" refers to the layer thickness of the printable composition upon deposition from a three-dimensional (3D) printing system. The printable composition may have a resolution of about 100 microns or less. The printable composition may have a resolution of less than about 100 microns, less than about 90 microns, less than about 80 microns, less than about 70 microns, less than about 60 microns, less than about 50 microns, less than about 40 microns, less than about 30 microns, less than about 20 microns, less than about 10 microns, less than about 5 microns, less than about 1 micron, or any range including and/or in between any two of these values. For example, in any embodiment herein, the printable composition may have a resolution of less than about 100 microns, and may preferably have a resolution of less than about 1 micron.

As used herein, the term "photo speed" refers to cure depth vs exposure energy, and is used to determine Dp/Ec of the printable composition. "Dp" (mm) refers to the cure depth of the printable composition, and "Ec" (mJ/cm$^2$) refers to the critical energy needed to convert the printable composition from liquid to the gel stage on the surface of the printable composition. In any embodiment herein, the cure depth (Dp) may include, but is not limited to, depths from about 0.1 mm to about 5 mm. For example, suitable cure depths (Dp) may include about 0.1 mm, about 0.2 mm, about 0.3 mm, about 0.4 mm, about 0.5 mm, about 0.6 mm, about 0.7 mm, about 0.8 mm, about 0.9 mm, about 1.5 mm, about 2.0 mm, about 2.5 mm, about 3.0 mm, about 3.5 mm, about 4.0 mm, about 4.5 mm, about 5.0 mm, or any range including and/or in between any two of these values. In any embodiment herein, the exposure energy may include, but is not limited to, amounts from about 10 mJ/cm$^2$ to about 100 mJ/cm$^2$. For example, suitable exposure energy amounts include about 10 mJ/cm$^2$, about 15 mJ/cm$^2$, about 20 mJ/cm$^2$, about 25 mJ/cm$^2$, about 30 mJ/cm$^2$, about 35 mJ/cm$^2$, about 40 mJ/cm$^2$, about 45 mJ/cm$^2$, about 50 mJ/cm$^2$, about 55 mJ/cm$^2$, about 60 mJ/cm$^2$, about 65 mJ/cm$^2$, about 70 mJ/cm$^2$, about 75 mJ/cm$^2$, about 80 mJ/cm$^2$, about 85 mJ/cm$^2$, about 90 mJ/cm$^2$, about 95 mJ/cm$^2$, about 100 mJ/cm$^2$, or any range including and/or in between any two of these values.

The term "green strength" refers to an initial cure hardening strength of the printable composition when initially exposed to curative radiation. The cure hardening strength can be quantified by measures such as elastic modulus and elongation before break. After drying or curing, the printable composition may exhibit a green strength of at least about 5 kPa, about 10 kPa, about 20 kPa, about 30 kPa, about 40 kPa, about 50 kPa, about 60 kPa, about 70 kPa, about 80 kPa, about 90 kPa, about 100 kPa, about 110 kPa, about 120 kPa, about 130 kPa, about 140 kPa, about 150 kPa, about 160 kPa, about 170 kPa, about 180 kPa, about 190 kPa, about 200 kPa, or any range including and/or in between any two of these values. For example, in any embodiment herein, after curing, the printable composition may exhibit a green strength of about 5 kPa to about 200 kPa, about 5 kPa to about 100 kPa, about 5 kPa, to about 50 kPa, about 5 kPa to about 25 kPa, or may preferably exhibit a green strength of about 5 kPa to about 10 kPa.

In any embodiment herein, the one or more collagens may include collagens functionalized with a monomeric subunit. Suitable monomeric subunits include water soluble monomers. For example, in any embodiment herein, the water soluble monomeric subunits may include one or more acrylic monomers. Suitable acrylic monomers include acrylate, methacrylate, acrylamide, methacrylamide, N-hydroxyethyl acrylamide (HEAA), hydroxyethyl methacrylate (HEMA), hydroxyethyl acrylate (HEA), monomers having a thiol, amine, epoxide, azido, alkyne, or N-hydroxyl succinimide reactive group, or combinations of two or more thereof. In any embodiment herein, the water soluble monomeric subunits may include other unsaturated monomers. Suitable monomers include vinyl monomers, monomers formed from maleic anhydride or acid, acryloyl morpholine (ACMO), N-vinylpyrrolidone (NVP), N-vinylcaprolactam (V-CAP), or the like and combinations thereof.

The one or more collagens may include a mixture of a first collagen and a second collagen, where the first collagen is a functionalized collagen as described herein in any embodiment, and the second collagen is a non-functionalized collagen. In any embodiment herein, the first collagen and second collagen may be present at a weight ratio of at least about 99:1 to about 1:99 based on dry weight of the collagen. For example, in any embodiment herein, the weight ratio of the first collagen and second collagen may include, but is not limited to, a weight ratio of at least about 99:1, about 50:1, about 25:1, about 10:1, about 5:1, about 2:1, about 1:1, about 1:2, about 1:5, about 1:10, about 1:25, about 1:50, about 1:99, or any range including and/or in between any two of these values.

The one or more collagens may be from a mammalian source. Suitable mammalian sources include, but are not limited to, equine, canine, porcine, bovine, feline, caprine, ovine, murine, human, or combinations of two or more thereof. For example, in any embodiment herein, the one or more collagens may be bovine collagen, porcine collagen, or human collagen.

In any embodiment herein, the one or more collagens may include recombinant collagens. As described herein, the term "recombinant collagen" refers to collagen obtained from a recombinant source. The recombinant source may include recombinant mammalian collagen produced from plants, bacteria, viruses, fungi, or the like and combinations of two or more thereof. For example, in any embodiment herein, the recombinant collagen may include recombinant human collagen, recombinant bovine collagen, recombinant porcine collagen, or combinations of two or more thereof. In some embodiments, the recombinant source includes recombinant mammalian collagen produced from a plant source, including but not limited to, tobacco. In some embodiments, the printable composition may include a recombinant collagen functionalized with one or more acrylic monomers, including but not limited to, acrylate, methacrylate, acrylamide, methacrylamide, monomers having a thiol, amine, epoxide, azido, alkyne, or N-hydroxyl succinimide reactive group, or combinations of two or more thereof.

The one or more collagens may include any type of collagen. For example, in any embodiment herein, the one or more collagens may be type I collagen. Type I collagen can be found in most connective tissues, is the most abundant collagen type in a living organism. Over 90% of the collagen in the body is type I.

In any embodiment herein, the one or more collagens may be present in an amount from about 0.3 weight percent (wt %) to about 3.0 wt % by weight of the printable composition. Thus, the one or more collagens may be included in an amount of about 0.3 wt %, about 0.4 wt %, about 0.5 wt %, about 0.6 wt %, about 0.8 wt %, about 0.9 wt %, about 1.0 wt %, about 1.5 wt %, about 2.0 wt %, about 2.5 wt %, about 3 wt %, or any range including and/or in between any two of these values. For example, in any embodiment herein, the printable composition may include one or more collagens in an amount of about 0.3 wt % to about 3.0 wt %, about 0.5 wt % to about 3.0 wt %, or about 0.3 wt % to about 0.9 wt % by weight of the printable composition. In some embodiments, the printable composition may include about 0.5 wt % to about 3.0 wt % of recombinant collagen. In some embodiments, the printable composition may include about 0.3 wt % to about 0.9 wt % collagen from a mammalian source.

The printable composition includes one or more monomers. For example, in any embodiment herein, the printable composition may include an acrylic monomer. Suitable monomers include, but are not limited to, N-hydroxyethyl acrylamide (HEAA), 2-hydroxyethyl methacrylate, poly(ethylene glycol) diacrylate, polyethylene glycol dimethacrylate (PEGDMA), polycaprolactone dimethacrylate, polycaprolactone trimethacrylate, or a mixture of two or more thereof. In some embodiments, the monomer may be N-hydroxyethyl acrylamide (HEAA).

The one or more monomers may be present in an amount from about 5.0 wt % to about 40.0 wt % by weight of the printable composition. Suitable amounts include, but are not limited to, about 5.0 wt %, about 10 wt %, about 15 wt %, about 20 wt %, about 25 wt %, about 30 wt %, about 35 wt %, about 40 wt %, or any range including and/or in between any two of these values. For example, in any embodiment herein, the printable composition may include from about 10 wt % to about 40 wt %, about 15 wt % to about 40 wt %, about 20 wt % to about 40 wt %, or about 30 wt % to about 40 wt % of the one or more monomers.

The printable composition includes a photo initiator. The photo initiator is a radiation activated catalyst (i.e., activated upon exposure to UV, violet, or blue radiation) for at least polymerizing and/or cross-linking the monomer. Suitable photo initiators may include, but are not limited to, 2-hydroxy-4'-(2-hydroxyethoxy)-2-methylpropiophenone, ethyl (2,4,6-trimethylbenzoyl) phenylphosphinate, phenyl bis(2,4,6-trimethylbenzoyl)phosphine oxide, diphenyl(2,4,6-trimethylbenzoyl)phosphine oxide, or combinations of two or more thereof. For example, in any embodiment herein, the photo initiator may include diphenyl(2,4,6-trimethylbenzoyl)phosphine oxide.

The photo initiator may be present in an amount from about 0.5 wt % to about 2.0 wt % of the printable composition. Suitable amounts include, but are not limited to, about 0.5 wt %, about 0.6 wt %, about 0.7 wt %, about 0.8 wt %, about 0.9 wt %, about 1.0 wt %, about 1.2 wt %, about 1.5 wt %, about 1.8 wt %, about 2.0 wt %, or any range including and/or in between any two of these values. For example, in any embodiment herein, the printable composition includes about 0.5 wt % to about 2.0 wt %, about 0.7 wt % to about 1.8 wt %, about 1 wt % to about 1.5 wt % of photo initiator.

The printable composition of the present technology includes a vehicle that includes a protic solvent. Protic solvents as used herein include, but are not limited to, water, alcohols (e.g., methanol (CH3OH), ethanol (EtOH), isopropanol (iPrOH), trifluoroethanol (TFE), butanol (BuOH), ethylene glycol, propylene glycol), carboxylic acids (e.g., formic acid, acetic acid, propanoic acid, butanoic acid, pentanoic acid, lauric acid, stearic acid, deoxycholic acid, glutamic acid, glucuronic acid), ammonia (NH3), a primary amino compound, (e.g., methyl amine, ethyl amine, propyl amine), a secondary amino compound (e.g., dimethyl amine, diethyl amine, di(n-propyl amine), or a mixture of any two or more thereof. Thus, in any of the embodiments and aspects herein, the protic solvent may include an alcohol, a carboxylic acid, a primary amino compound, a secondary amino compound, water, or a mixture of any two or more thereof. In any embodiment herein, the protic solvent may include water, such as deionized water. The amount of vehicle in the printable composition may be 0 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt % about 70 wt %, about 75 wt %, or any range including and/or in between any two of these values. In particular, the amount of water in the vehicle may be about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt % about 70 wt %, about 75 wt %, about 80 wt %, about 85 wt %, about 90 wt %, about 95 wt %, about 99 wt %, or any range including and/or in between any two of these values.

The printable composition includes a vehicle that contains water. The vehicle may further include a water-soluble acrylic monomer. For example, in any embodiment herein, the water-soluble acrylic monomer includes, but is not limited to, carboxyethyl acrylate, poly(alkylene)(meth)acrylates (e.g., poly(ethylene glycol) diacrylate or polyethylene glycol dimethacrylate (PEGDMA)), HEAA, HEMA, HEA, ACMO, NVP, V-CAP, or combinations of two or more thereof. The vehicle may further include a carboxylic acid as described herein. For example, in any embodiment herein, the carboxylic acid may include, but is not limited to, formic acid, acetic acid, propanoic acid, butanoic acid, pentanoic acid, lauric acid, stearic acid, deoxycholic acid, glutamic acid, glucuronic acid, or a combination of two or more thereof. In particular embodiments, the carboxylic acid may be acetic acid. The concentration of the carboxylic acid may be from about 5 mM to about 200 mM. For example, in any embodiment herein, the concentration of carboxylic acid may be about 5 mM, about 10 mM, about 15 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, or any range including and/or in between any two of these values.

In any embodiment herein, the printable composition may have a pH of about 2. Suitable pH values for the printable composition may include, but are not limited to, about 2, about 3, about 4, about 5, about 6, about 7, or any range including and/or in between any two of these values.

The printable composition may further include one or more photobase generators. Suitable photobase generators may include, but are not limited to, carbamates, O-acyloximes, ammonium salts, sulfonamides, formamides, nifedipines, transition metal complexes, metallocenes, aminie-imide, or alpha-aminoketones. For example, in any embodiment herein, the photobase generators may include, but are not limited to, 9-anthylmethyl N,N-diethylcarbamate, (E)-1-piperidino-3-(2-hydroxyphenyl)-2-propen-1-one, 1-(anthraquinon-2-yl)ethyl imidazole carboxylate, 2-nitrophenyl methyl 4-methacryloyloxy piperidine-1-carboxylate, 1,2-diisopropyl-3-[bis(dimethylamino)methylene] guanidinium-2-(3-benzoylphenyl) propionate, 1,2-dicyclohexyl-4,4,5,5-tetramethylbiguanidium N-butyltriphenylborate, (Z)-{[bis(dimethylamino)methylidene]amino}-N-cyclohexyl(cyclohexylamino) methaniminium tetrakis(3-fluorophenyl)borate, or combinations of two or more thereof.

In any embodiment herein, the printable composition may include a functionalized collagen, an acrylate monomer, photo initiator, a vehicle, and a photobase generator, where the functionalized collagen includes a collagen functionalized with a methacrylate. The photobase generator may be present in an amount from 0 wt % to about 10 wt %. For example, in any embodiment herein, the photobase generator may be present an amount from 0 wt %, 0.01 wt %, about 0.1 wt %, about 0.5 wt %, about 1 wt %, about 2 wt %, about 3 wt %, about 4 wt %, about 5 wt %, about 6 wt %, about 7 wt %, about 8 wt %, about 9 wt %, about 10 wt %, or any range including and/or in between any two of these values. Suitable amounts of photobase generator include from about 0 wt % to about 10 wt %, about 0 wt % to about 9 wt %, about 0 wt % to about 7 wt %, 0 wt % to about 3 wt %, or any range including and/or in between any two of these values.

In any embodiment herein, the printable composition may include a non-functionalized collagen, an acrylate monomer, photo initiator, a vehicle, and a photobase generator. In any embodiment herein, the printable composition may include a functionalized collagen, a non-functionalized collagen, photo initiator, a vehicle, and photobase generator, where the functionalized collagen includes a collagen functionalized with a methacrylate.

The printable composition may further include one or more absorbers. For example, in any embodiment herein, absorbers include, but are not limited to, absorbers having greater than 0.1 absorbance units at wavelengths between about 300 nm to about 450 nm. For example, in any embodiment herein, the absorbers may have an absorbance at wavelengths between about 300 nm to about 450 nm from about 0.1 to about 0.7 absorbance units, about 0.1 to about 0.5 absorbance units, or about 0.1 to about 0.3 absorbance units. Suitable absorbance values include absorbance units of about 0.1, about 0.2, about 0.3, about 0.4, about 0.5, about 0.6, about 0.7, or any range including and/or in between any two of these values. In any embodiment herein, the absorbers may include absorbers having greater than 0.1 absorbance units at wavelengths from about 300 nm to about 405 nm. For example, in any embodiment herein, the absorbers may include, but are not limited to, tartrazine. The absorber may be present in an amount from 0 wt % to about 1.0 wt %. For example, in any embodiment herein, the amount of absorber is from 0 wt % to about 1.0 wt %, from about 0.1 wt % to about 0.8 wt %, or from about 0.3 wt % to about 0.7 wt %.

In any embodiment herein, the printable composition may include a functionalized collagen, an acrylate monomer, photo initiator, a vehicle, and an absorber, where the functionalized collagen includes a collagen functionalized with a methacrylate. In any embodiment herein, the printable composition may include a non-functionalized collagen, an acrylate monomer, a photo initiator, and an absorber. In any embodiment herein, the printable composition may include a functionalized collagen, a non-functionalized collagen, an acrylate monomer, photo initiator, a vehicle, and an absorber, where the functionalized collagen includes a collagen functionalized with a methacrylate.

In some embodiments, the printable composition may include a functionalized collagen, an acrylate monomer, photo initiator, a vehicle, a photobase generator, and an absorber, where the functionalized collagen includes a collagen functionalized with a methacrylate. In some embodiments, the printable composition may include a non-functionalized collagen, an acrylate monomer, a photo initiator, a photobase generator, and an absorber. In some embodiments, the printable composition may include a functionalized-collagen, non-functionalized collagen, acrylate monomer, photo initiator, vehicle, photobase generator, and an absorber, where the functionalized-collagen includes a collagen functionalized with a methacrylate.

In a related aspect of the present technology, a method is provided for preparing a three-dimensional cell-receiving scaffold using the printable composition described herein in any embodiment. The method includes using the printable composition of any embodiment herein to fabricate a three-dimensional cell-receiving scaffold. For example, in any embodiment herein, the method may include fabricating a three-dimensional cell-receiving scaffold of an organ of a patient. As used herein, the term "subject" or "patient" is a mammal, such as a cat, dog, rodent, or primate. Typically, the subject or patient is human, and preferably in need of transplants or implants for tissue regeneration. The term "subject" and "patient" can be used interchangeably.

Fabricating the three-dimensional cell-receiving scaffold may include injection molding, rotational molding, positive molds, negative molds, subtractive manufacturing, or three-dimensional (3D) printing methods. In any embodiment herein, fabricating the three-dimensional cell-receiving scaffold may include 3D printing methods. The 3D printing methods may include additive manufacturing methods. Suitable additive manufacturing methods include ink jet printing, extrusion printing, or layer-by-layer printing. In any embodiment herein, fabricating the three-dimensional cell-receiving scaffold may include layer-by-layer printing methods.

In another related aspect of the present technology, a method is provided for manufacturing a three-dimensional cell-receiving scaffold that includes depositing a layer of the printable composition as described herein in any embodiment to a surface to obtain a deposited layer, irradiating the deposited layer, and repeating the depositing and irradiating steps until the deposited layers form the three-dimensional cell-receiving scaffold, where the printable composition includes collagen, where the collagen is present in an amount from about 0.3 percent to about 3.0 percent by weight of the printable composition; a monomer; a photo initiator; and a vehicle. The printable composition may include a printable composition as described herein in any embodiment.

The method includes depositing the printable composition to a surface. In any embodiment herein, the surface may include, but is not limited to, a surface of a system for use in 3D printing methods as described herein in any embodiment. Such systems include 3D printing systems for 3D printing methods including but not limited to ink jet printing, extrusion printing, or layer-by-layer printing. In any embodiment herein, the method may further include heating the printable composition to a temperature of 0° C. to about 30° C. prior to depositing. For example, in any embodiment herein, the printable composition may be heated to a temperature of 0° C., about 5° C., about 10° C., about 15° C., about 20° C., about 25° C., about 30° C., or any range including and/or in between any two of these values.

The method of the present technology includes irradiating the deposited layer to cure the printable composition. Irradiating the deposited layer may be carried out via exposure to ultraviolet (UV), violet, or blue radiation to cure the deposited layer. For example, in any embodiment herein, irradiating the deposited layer includes exposure to radiation at a wavelength from about 240 nm to about 405 nm. Suitable wavelengths may include, but are not limited to, about 240 nm to about 405 nm, about 240 nm to about 355 nm, about 240 nm to about 340 nm, about 240 nm to about 270 nm, or any range including and/or in between any two of these values. For example, in any embodiment herein, the wavelength may be about 270 nm or 355 nm.

In any embodiment herein, the deposited layer after irradiation has a resolution of at least 100 microns. After irradiation to cure the deposited layer of the printable composition, the deposited layer may have a resolution of less than about 100 microns, less than about 90 microns, less than about 80 microns, less than about 70 microns, less than about 60 microns, less than about 50 microns, less than about 40 microns, less than about 30 microns, less than about 20 microns, less than about 10 microns, less than about 5 microns, less than about 1 micron, or any range including and/or in between any two of these values. For example, in any embodiment herein, the deposited layer may have a resolution of less than about 100 microns, and may preferably have a resolution of less than about 1 micron.

Following the depositing and irradiating steps, the method includes repeating the deposition and irradiation steps until the deposited layers form the three-dimensional cell-receiving scaffold. Prior to repeating the depositing and irradiating steps, any uncured portions of the deposited layer may be removed before depositing and irradiating subsequent layers of the printable composition. For example, in any embodiment herein, the method further includes removing uncured printable composition after irradiation of the deposited layer and before repeating the deposition and irradiation steps.

In any embodiment herein, the method may further include contacting the three-dimensional cell-receiving scaffold with a low pH solution. While not being bound by theory, the low pH solution hydrolyzes ester linkages in the cured printable composition to improve cellularization of the three-dimensional cell-receiving scaffold. Thus, the green strength of the three-dimensional cell-receiving scaffold is lowered, making the scaffold more compatible for subsequent cellularization processes. In any embodiment herein, the pH of the low pH solution is less than about 7. Suitable pH values for the low pH solution may include, but are not limited to, less than about 6, less than about 5.5, less than about 5, less than about 4.5, less than about 4.0, less than about 3.5, less than about 3.0, less than about 2.5, less than about 2.0, or any range including and/or in between any two of these values.

Figure 2:
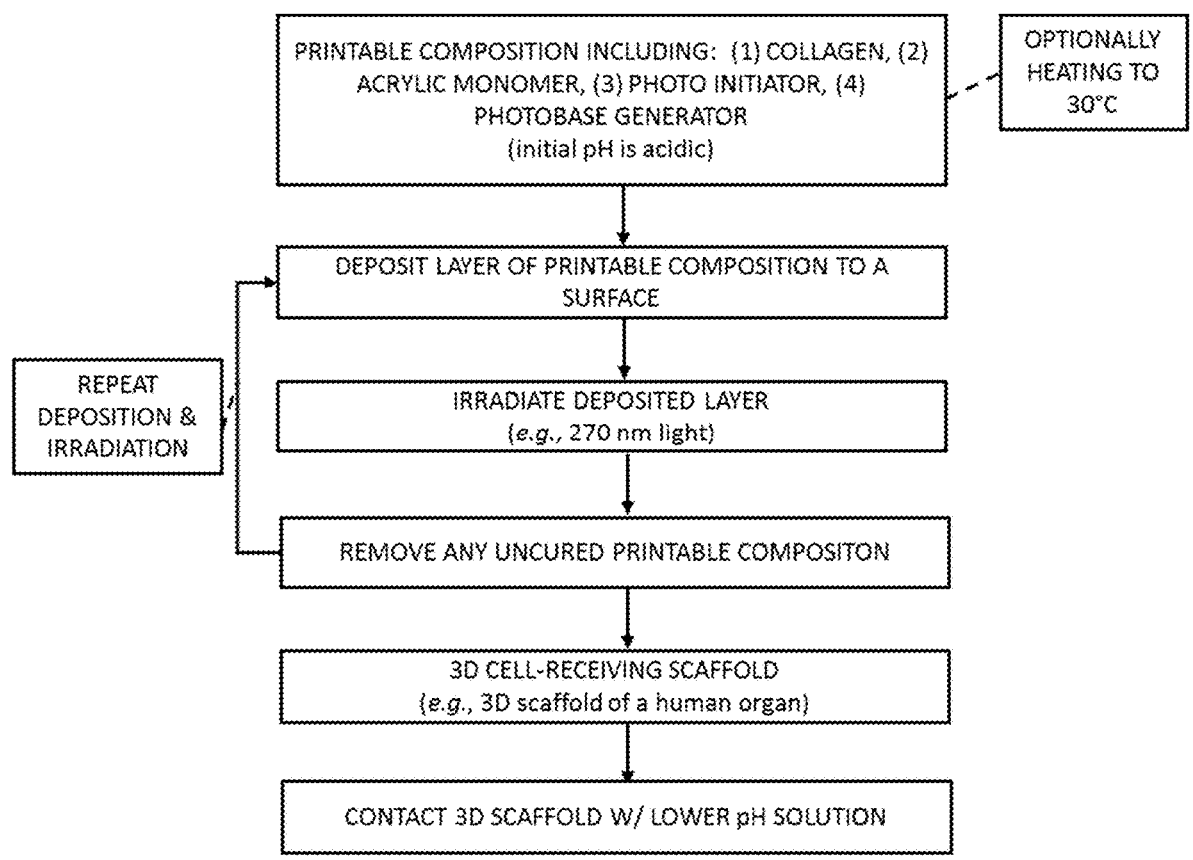
FIG. 2 illustrates a flowchart depicting an exemplary method for preparing a three-dimensional cell-receiving scaffold of the present technology that includes contacting the scaffold with a low pH solution.

In any embodiment herein, the method may further include contacting the three-dimensional cell-receiving scaffold with cells, tissues, growth factors, laminin, elastin, fibronectin, proteoglycans, hyaluronic acid, polysaccharides or a mixture of two or more thereof. For example, in any embodiment herein, the three-dimensional scaffold may be contacted with chondroitin sulfate proteoglycan, heparin sulphate proteoglycan, sulfated polysaccharides, carrageenan, agarose, polydextran, matrigel, or combinations of two or more thereof. Suitable cells, tissues, or growth factors may include, but are not limited to, transforming growth factor beta (TGF-β), epidermal growth factor like (EGF-like) domain, vascular endothelial growth factor (VEGF), platelet-derived growth factor (PGDF), Wnt family proteins, stromal cell-derived factor 1, vascular cells, epithelial cells, mesenchymal cells, or combinations of two or more. In at least one embodiment, the method of the present technology is a method according to the steps illustrated in FIG. 1. In at least another embodiment, the method of the present technology is a method according to the steps illustrated in FIG. 2.

The present invention, thus generally described, will be understood more readily by reference to the following examples, which are provided by way of illustration and are not intended to be limiting of the present invention.

EXAMPLES

Example 1: Printable Composition Formulations

Exemplary printable compositions were prepared according to Formulations A-F. Table 1 provides the amount of collagen, monomer, photo initiator, and vehicle included in each formulation. N-hydroxyethyl acrylamide (HEAA), polyethylene glycol dimethacrylate (PEGDMA 600), and tartrazine were purchased from Aldrich Corporation. Methacrylate functionalized bovine collagen was purchased from ABM Corporation. Human recombinant collagen from transgenic tobacco was purchased from CollPlant Ltd. The diphenyl(2,4,6-trimethylbenzoyl)phosphine oxide photo initiator was obtained from IGN Resin Corporation under the product name Omnirad TPO-L. All weight percentages are determined based on dry weight compared to the total weight of the ink formulation.

Formulation A: Formulation A was prepared by combining (1) a mixture of 100 mg of methacrylate functionalized bovine collagen and 10 mg of 20 mM acetic acid solution, (2) 100 mL of HEAA, (3) 3.38 g of tartrazine with 96 g of HEAA, (4) 1 L of PEGDMA 600, and diphenyl(2,4,6-trimethylbenzoyl)phosphine oxide (photo initiator). About 60 wt % of Formulation A is the methacrylate functionalized collagen in 20 mM acetic acid solution, which is about 1% collagen by weight. Therefore, Formulation A includes about 0.6% collagen by dry weight. Formulation A includes about 10-15% HEAA monomer by weight. Formulation A has the advantage of providing a high green strength while still having a large collagen component. When used as a printable composition, Formulation A yielded 1-15 cm three-dimensional objects exhibiting a green strength in the range of 1-50 kPa.

In terms of weight percentages (wt %), Formulation A includes 59.7 wt % methacrylate bovine collagen in 20 mM acetic acid, 0.71 wt % tartrazine, 36.91 wt % HEAA, 1.49 wt % PEGDMA, and 1.19 wt % diphenyl(2,4,6-trimethylbenzoyl)phosphine oxide. Component (1) can be expressed as subcomponents including (1A) 59.11 wt % 20 mM acetic acid and (1B) 0.59 wt % methacrylate bovine collagen.

Formulation B: Formulation B was prepared by combining 60.59 wt % of a mixture of methacrylate bovine collagen in aqueous carboxyethyl acrylate solution, (2) 38.20 wt % HEAA, and 1.21 wt % of diphenyl(2,4,6-trimethylbenzoyl)phosphine oxide photo initiator. The dry weight percentage of methacrylate bovine collagen is 0.6 wt %. This formulation has an advantage of a high photo speed and green strength. The photo speed of Formulation B was sufficient to permit z-layer prints over an area of 80 cm2 in less than 3 s, and Formulation B exhibited a green strength of 20 kPa.

Formulation C: Formulation C was prepared by combining 59.88 wt % of a mixture of methacrylate bovine collagen in carboxyethyl acrylate water solution, 16.6 wt % of type I bovine collagen solution in acetic acid, 22.5 wt % HEAA, and 1 wt % 2 diphenyl(2,4,6-trimethylbenzoyl)phosphine oxide. The dry weight percentage of methacrylate bovine collagen is 0.59 wt %. Relative to Formulation B, this formulation may improve certain cell growing processes due to the addition of the non-functionalized bovine collagen.

Formulation D: Formulation D was prepared by combining 71.4 wt % of a mixture of methacrylate bovine collagen in carboxyethyl acrylate water solution, 17.9 wt % of type I bovine collagen solution in acetic acid, 7.14 wt % PEGDMA 600, 2.86 wt % HEAA, and 0.71 wt % diphenyl(2,4,6-trimethylbenzoyl)phosphine oxide. The dry weight percentage of methacrylate bovine collagen is 0.71%. The higher collagen content may benefit certain cell growing processes.

Formulation E: Formulation E was prepared by combining 61.35 wt % of methacrylate bovine collagen in 20 mM acetic acid, 23.31 wt % of type I bovine collagen solution in acetic acid, (3) 14.11 wt % HEAA, and 1.22 wt % diphenyl (2,4,6-trimethylbenzoyl)phosphine oxide. The dry weight percentage of methacrylate bovine collagen is 0.61 wt %.

Formulation F: Formulation F was prepared by combining 61.35 wt % human recombinant collagen (produced from tobacco plants) solution, 23.31 wt % of type I bovine collagen solution in acetic acid, 14.11 wt % HEAA, and) 1.22 wt % diphenyl(2,4,6-trimethylbenzoyl)phosphine oxide.

Formulation G: 94.34 wt % of recombinant human collagen in 20 mM acetic acid, (2) 4.53 wt % of methanol, and (3) 1.13 wt % of 2 diphenyl(2,4,6-trimethylbenzoyl)phosphine oxide. The dry weight of the collagen is 1.39 wt %.

TABLE 1

| Component | A | B | C | D | E | F | G |
|---|---|---|---|---|---|---|---|
| Methacrylated Bovine Collagen (wt %) | 0.59 | 0.6 | 0.59 | 0.71 | 0.61 | 0 | 0 |
| Type 1 Bovine Collagen Solution (wt %) | 0 | 0 | 16.63 | 17.86 | 23.31 | 23.31 | 0 |
| Plant-Based (Human Recombinant) Collagen Solution (wt %) | 0 | 0 | 0 | 0 | 0 | 61.35 | 94.34 |
| HEAA (wt %) | 36.91 | 38.20 | 22.49 | 2.86 | 14.12 | 14.11 | 0 |
| PEG Dimethacrylate 600 (wt %) | 1.49 | 0 | 0 | 7.14 | 0 | 0 | 0 |
| TPO-L (wt %) | 1.19 | 1.21 | 1 | .71 | 1.22 | 1.23 | 1.13 |
| Tartrazine (wt %) | 0.71 | | 0 | 0 | 0 | 0 | 0 |
| Vehicle (wt %) | 59.11 | 59.99 | 59.29 | 70.72 | 60.74 | 0 | 0 |
| Methanol (wt %) | 0 | 0 | 0 | 0 | 0 | 0 | 4.53 |
| Total Wt % | 100 | 100 | 100 | 100 | 100 | 100 | 100 |

All numbers are the weight percent based on the total weight of printable composition.

Example 2: Evaluation of Cell Viability

Figure 3:
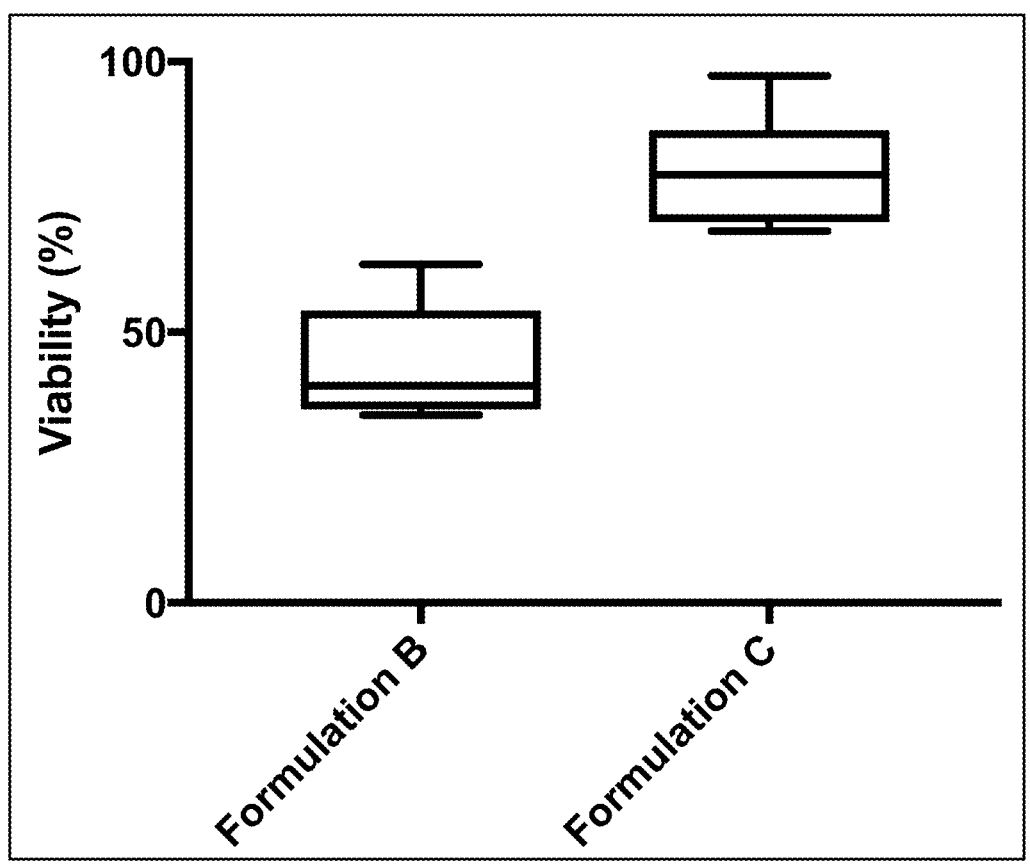
FIG. 3 illustrates the viability of human epithelial lung carcinoma cells over 48 h in three-dimensional scaffolds of Formulation B and Formulation C.

Human epithelial lung carcinoma cells (A549, ATCC, CCL-185) were used to evaluate cell viability. Cells were maintained in F-12K medium (Kaighn's modification, ATCC) supplemented with 10% FBS, 50 µg mL$^{-1}$ penicillin, 50 µg mL$^{-1}$ streptomycin. Formulations were prepared as described above for Formulations B and C and cured in a 96-well plate using an ultraviolet oven. 6000 cells were seeded per each well and incubated at 37° C. in 5% $CO_2$. After 48 hours of incubation in each indicated printed formulation, cells were gently washed three times with PBS and cytotoxicity assessment was performed using PicoGreen assay according to the manufacturer's instructions (Life Technologies, Thermo Fisher Scientific). Formulation C exhibited 80% cell viability 48 h after cell seeding (FIG. 3).

Example 3: Preparation of a Three-Dimensional Cell-Receiving Scaffold

An acidic printable composition according to Formulation H was used to prepare a three-dimensional cell-receiving scaffold. Formulation H was prepared according to the preparation methods described in Example 1 and as described in Table 2 below.

TABLE 2

| Formulation H | Amount (wt %) |
|---|---|
| 10 mg/1 g 20 mM Acetic Acid, Coll-MA Collagen (human recombinant collagen) | 37.50 |
| 20 mM Acetic acid | 8.33 |
| MIX-3 (3.4% tartrazine/96.6% HEAA) | 9.17 |

TABLE 2-continued

| Formulation H | Amount (wt %) |
|---|---|
| HEAA | 33.33 |
| PEG 600 DIMA | 3.33 |
| TPO-L/HEAA (4/16) | 8.33 |
| Total | 100 |

Figure 4:
FIG. 4 illustrates a three-dimensional scaffold printed using a printable composition according to Formulation H.

A layer of uncured printable composition was deposited to a surface vertically positioned to receive the layer of ink. The deposited layer of printable composition was irradiated at a wavelength of 355 nm, having a resolution of <100 microns. The deposition and irradiating steps were repeated until the scaffold was fully formed. FIG. 4 shows the resulting three-dimensional scaffold obtained from printing of the printable composition according to Formulation H.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of manufacturing a three-dimensional cell-receiving scaffold comprising:
    depositing a layer of a printable composition to a surface to obtain a deposited layer;
    irradiating the deposited layer;
    repeating the depositing and irradiating steps until the deposited layers form the three-dimensional cell-receiving scaffold; and
    contacting the three-dimensional cell-receiving scaffold with an acidic solution that hydrolyzes ester linkages in the printable composition to lower a green strength of the three-dimensional cell-receiving scaffold;
    wherein the printable composition comprises collagen, wherein the collagen is present in an amount from about 0.3 percent to about 3.0 percent by weight of the printable composition; a monomer; a photo initiator; and a vehicle.

2. The method according to claim 1, wherein the printable composition is a printable composition for manufacturing cell-receiving scaffolds comprising:
    about 5.0 wt % to about 40.0 wt % of the monomer;
    about 0.5 wt % to about 2.0 wt % of the photo initiator; and
    0.1 wt % to about 75 wt % of the vehicle comprising a protic solvent, by weight of the printable composition;
    wherein the printable composition has a resolution of about 100 microns or less when printed, a photo speed (Dp/Ec) of about 0.1-5 mm (Dp) and about 10-100 mJ/cm$^2$ (Ec) when printed, and the green strength of at least about 5 kPa after drying.

3. The method according to claim 1 wherein the method further comprises heating the printable composition to a temperature of 0° C. to about 30° C. prior depositing.

4. The method according to claim 1, wherein the method further comprises contacting the three-dimensional cell-receiving scaffold with cells, tissues, growth factors, laminin, elastin, fibronectin, proteoglycans, hyaluronic acid, polysaccharides, or a mixture of two or more thereof.

* * * * *